(12) United States Patent
Lucas et al.

(10) Patent No.: US 7,431,497 B2
(45) Date of Patent: Oct. 7, 2008

(54) DENTAL X-RAY FILM VIEWING DEVICE

(76) Inventors: James John Lucas, 100 Recovery Dr. West, Centreville, MD (US) 21617; Fereidon Wolfgang Manssuri, 24769 Pealiquor Rd., Denton, MD (US) 21629; Francis J. Lucas, 2143 Bethel Blvd., Boca Raton, FL (US) 33486

( * ) Notice: Subject to any disclaimer, the term of this patent is extended or adjusted under 35 U.S.C. 154(b) by 16 days.

(21) Appl. No.: 11/527,014

(22) Filed: Sep. 26, 2006

(65) Prior Publication Data

US 2008/0075231 A1   Mar. 27, 2008

(51) Int. Cl.
*A61B 6/14* (2006.01)
(52) U.S. Cl. .................. 378/168; 250/559.02
(58) Field of Classification Search ......... 378/167–170, 378/181, 38–40; 250/559.02
See application file for complete search history.

(56) References Cited

U.S. PATENT DOCUMENTS

| 4,013,833 | A | | 3/1977 | Zimmerman |
| 5,870,172 | A | * | 2/1999 | Blume ........................ 355/27 |
| 6,097,902 | A | * | 8/2000 | Blume ........................ 396/569 |
| 6,644,851 | B1 | * | 11/2003 | Kumagai ..................... 378/167 |
| 7,053,391 | B2 | * | 5/2006 | Blume .................... 250/559.02 |
| 2004/0073092 | A1 | | 4/2004 | Miles |
| 2006/0038141 | A1 | | 2/2006 | Blume |

* cited by examiner

*Primary Examiner*—Courtney Thomas
(74) *Attorney, Agent, or Firm*—Yi Li

(57) ABSTRACT

A dental x-ray film viewing device includes a film reader having a digital video camera and an image display screen connected to the video camera for displaying an enlarged digital image of the x-ray film using signals transmitted directly from the video camera. The film reader includes a film illumination station that has a back-lighted film seat. The film seat includes a translucent plate and a non-transparent film anchoring wafer having an opening complimentary to the x-ray film for seating the x-ray film, and blocking light in an area surrounding the x-ray film. The film reader has a video camera having lens thereof focusing on the film window, and the lens has a distortion at the full field less than 3%. The device provides a substantially enlarged high resolution and high contrast digital image as an accurate representation of the original x-ray film, without digital processing by a computer.

26 Claims, 6 Drawing Sheets

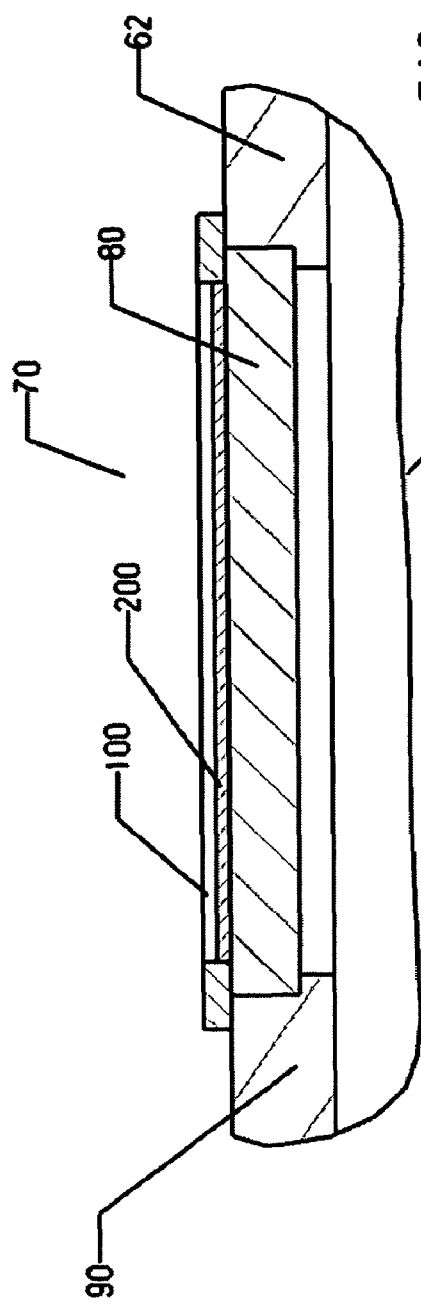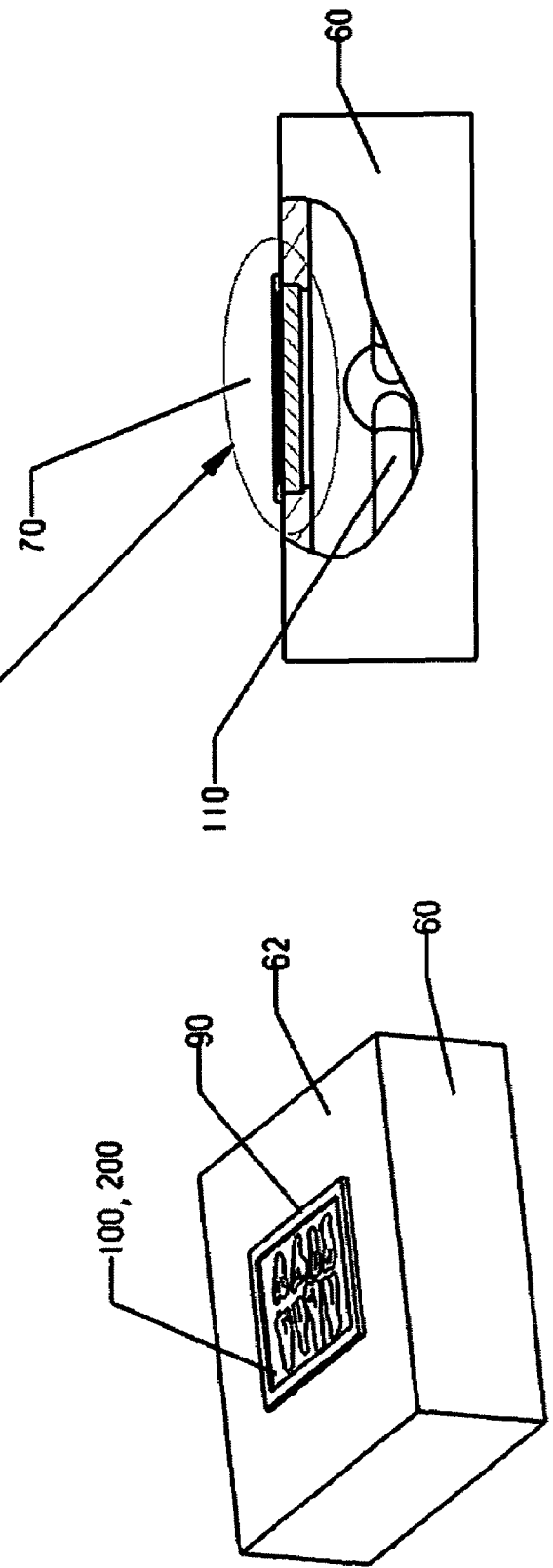

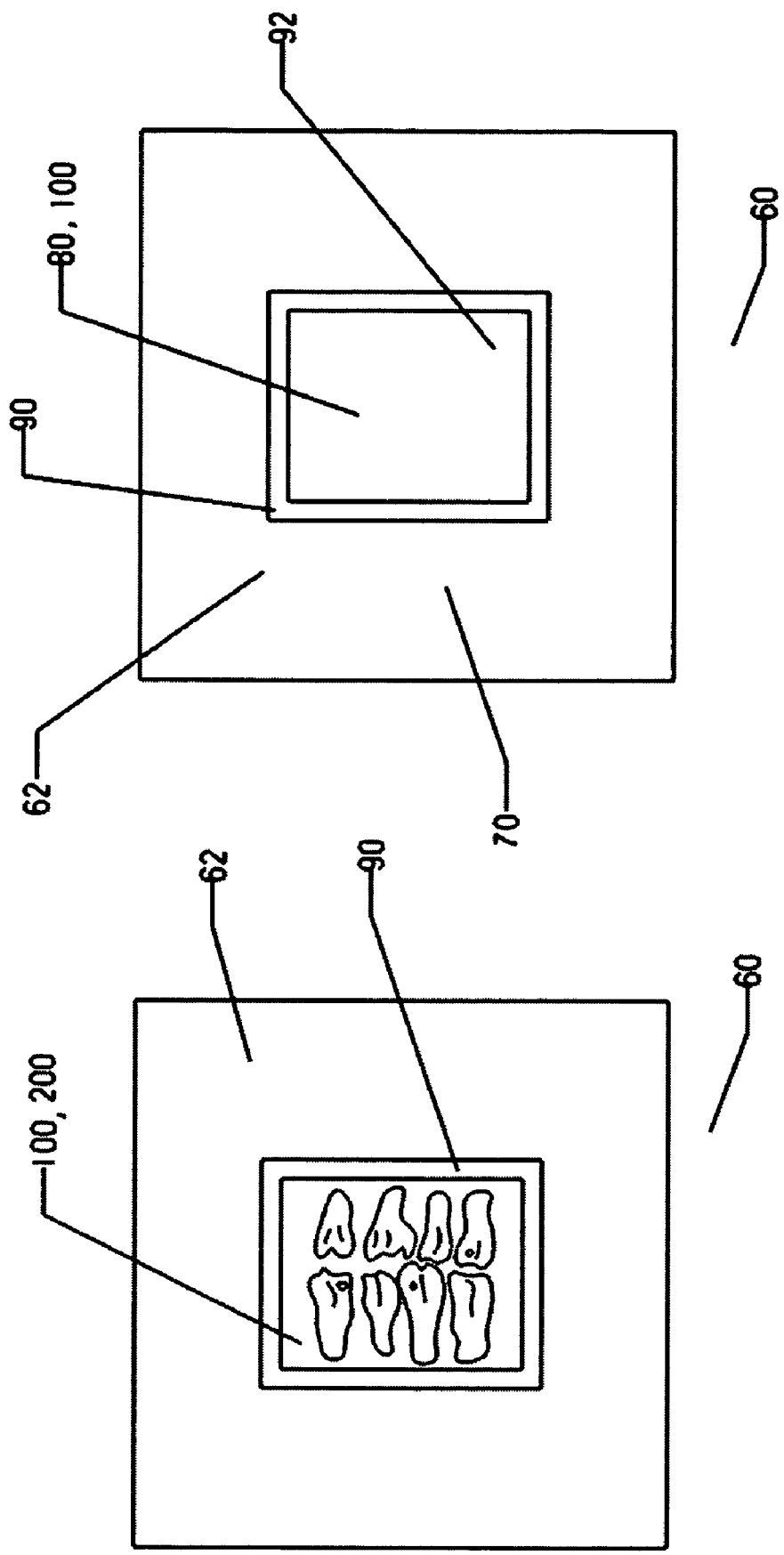

DENTAL X-RAY FILM VIEWING DEVICE

FIELD OF THE INVENTION

The present invention relates to a dental X-ray film viewing device. More specifically, the viewing device provides a substantially enlarged digital image of an entirety of an intra-oral x-ray film using signals transmitted directly from a video camera without digital processing by a computer.

BACKGROUND OF THE INVENTION

Intra-oral dental x-ray film is used in general dentistry and by some specialists. By necessity, these films must be small in order to be placed inside of the patients' mouth. Furthermore, the objects being radio-graphed, the patients' teeth, are also small. Consequently, the dental images are exceedingly small, making diagnosis and patient case presentation utilizing these x-ray films a difficult task. After obtaining the x-rays films, the dentist must examine them in order to determine if there are dental diseases to be treated. For example, the dentist identifies dental caries by noting dark (radiolucent) areas on the x-ray image, checks the bone density and levels, examines the roots and nerves of the teeth, checks the position and development of the teeth, looks for lesions such as cysts or tumors, assesses damage when trauma occurs, and monitors periodontal conditions. All assessment and diagnosis must be determined on a set of very small films, each of them has a standard size of 1 inch by 1.25 inch, or 1 inch by 3 inch. In the conventional practice, this is accomplished by clipping the film to a dental x-ray viewer light box for back-lighting the film for visual inspection. Although the x-ray film has very high resolution, the information revealed often is not sufficient for diagnosis or monitoring a dental treatment because of its small size.

With the advance of the digital image technology, several different types of devices have been developed to produce digital images of the intra-oral x-ray film for visual inspection by the dentist, and communication with the patients.

In one approach, direct digital imaging is used to provide enlarged digital images on a display screen. This technique utilizes a probe equipped with an x-ray sensing charged coupling device (CCD). During a dental examination, the probe is placed inside a patient's mouth, upon exposing to a small dose of x-rays, the image formed on the CCD device is sent to a computer where it is processed. The processed digital image can then be viewed on a computer screen, and can be manipulated and printed. To date, this is an exceedingly expensive technique, and the produced digital images do not have the same image clarity and quality of the x-ray film. Furthermore, as the digital image produced depends on the algorithm and software used by instrument, reliability of information provided still remains questioned by the dentists and the regulatory authorities. Up to date, none of these instruments has received U.S. Food and Drug Administration's approval as a diagnostic instrument.

In an other type of approach, several devices have been disclosed in the prior art, which capture images from the x-ray film by a video camera, and uses the digital images for displaying. Among most of them, the captured digital images are post processed by a computer using various digital processing techniques. U.S. Pat. No. 5,995,138 (to Beer, et al) teaches capturing the image from dental x-ray film through the use of a video camera. The digital image obtained by the video camera is sent to a computer to be digitized, for facilitating communication between dentists and insurance companies. U.S. Pat. No. 4,013,833 (to Zimmerman) teaches to use a video camera to capture x-ray film images projected onto a target plate.

U.S. Patent Application Publication No. 2006/0038141 A1 (Blume) teaches an apparatus for converting a standard dental x-ray view box into an analog or digital viewing system. The apparatus includes a Y-axis track and a X-axis track attached to the chassis of a standard dental x-ray view box, and a CCD video camera attached to the Y-axis track. The CCD video camera is movable in both Y and X axes for capturing images from multiple x-ray films clipped on the x-ray view box. The image is directly transmitted to and displayed on a monitor. As the CCD video camera is positioned very close to the x-ray films by the tracks, a quarter inch thick ruby-clear acrylic filter is used to reduce the intensity of the back light emitted from the x-ray view box. With this device, the back lighting of the x-ray view box directly sheds on to the camera, which causes poor contrast of the digital images produced. Furthermore, as can be appreciated, with such a shorter working distance, a substantial distortion of the digital image is inherent. Moreover, this typically produces an image with a focused center portion, but blurred edge portions, therefore, not the entirety of the enlarged image can be used for the purpose of diagnosis.

Commercially, a x-ray film viewer produced by DENTAMERICA™ is available under the product name Telerex Video X-ray Film Viewer. This device uses a video camera to capture the image of a standard x-ray film, which is transmitted directly to a TV or computer monitor for displaying an enlarged image. It is an inexpensive, compact equipment with a height of 9.4 cm. However, the quality of the digital images produced is poor. The enlarged digital image has blurred edges, and only the center of the x-film is in focus. In terms of the usefulness for diagnosis, only the distal portions of the image can not be used. For example, if the x-ray film has an image of five teeth, the teeth at the distal portions where the image has more distortion and poor resolution, can not be used by the dentist. Furthermore, this device uses a horizontal spring loaded film tray for carrying the film into the housing of the instrument. However, the film tray obstructs the edges of the x-film from displaying.

Based on the above, it is apparent that there is need for an inexpensive, reliable x-ray film viewing device which provides a substantially enlarged and undistorted digital image of the entirety of a standard intra-oral x-ray film with sufficient quality for diagnosis.

SUMMARY OF THE INVENTION

In one aspect, the present invention is directed to a dental X-ray film viewing device. In one embodiment, the dental X-ray film viewing device comprises a film reader and an image display screen. The film reader comprises a support panel, a film illumination station attached to a first end of the support panel, and a video camera attached to a second end of the support panel. The film illumination station comprises an illumination housing, a film seat on a wall of the housing, and a diffused white light source disposed within the illumination housing for backlighting the film seat. The film seat comprises a translucent plate and a non-transparent film anchoring wafer disposed against the translucent plate, the film anchoring wafer having an inner opening complimentary to an intra-oral x-ray film thereby forming a translucent film window for seating the x-ray film within the film window. The film anchoring wafer blocks light from the light source in an area surrounding the x-ray film. The video camera has a lens directed to the center of the film window of the film illumination station. The lens of the video camera has a distortion at full field less than 3%. The image display screen is connected to the video camera of the film reader by a cable, for displaying an enlarged digital image of the x-ray film using signals transmitted directly from the video camera.

Preferably, the lens of the video camera has a distortion at full field less than 1% and a working distance in a range from about 200 mm and about 400 mm; and the video camera has a resolution of at least 512×582 pixels. The image display screen is a LCD monitor having a resolution no less than the resolution of the video camera and a contrast ratio of at least 400:1.

The enlarged digital image provided by the instant device has an enlargement ratio from about 75:1 to about 150:1 ($in^2$:$in^2$). The enlarged digital image includes an entirety of the intra-oral x-ray film, and has a substantially equivalent resolution and contrast between a central portion and a distal portion of the image, and a distortion at full field less than 3%.

In a further embodiment, the dental X-ray film viewing device further comprises a system housing for shielding the stray light from the environment, and the support panel is disposed within and firmly attached to the housing. In one embodiment, the system housing has a film access opening, which has a light shielding rim surrounding the opening and protruding toward an interior of the system housing.

In a further aspect, the present invention is directed to a method of producing an enlarged digital image of an intra-oral x-ray film. In one embodiment, the method comprises the steps of: placing an intra-oral x-ray film on a translucent film window complementary in dimensions to the x-ray film, and backlighting the film window with a diffused white light source; the film window being surrounded by a non-transparent material to substantially block light from the light source in an area surrounding the x-ray film; positioning a video camera with a lens thereof directing to a center of the x-ray film, the lens having a distortion at full field less than 3% and the video camera having a resolution of at least 512×582 pixels; and displaying a substantially enlarged digital image of the x-ray film on an image display screen having a resolution no less than the resolution of the video camera, using signals transmitted directly from the video camera.

In yet another aspect, the present invention is directed a method of dental diagnosis. In one embodiment, the method comprises the steps of: providing an intra-oral x-ray film; focusing the lens of a video camera on the x-ray film wherein the lens has a distortion at full field less than 3% and the video camera has a resolution of at least 512×582 pixels; displaying a substantially enlarged digital image of the x-ray film on an image display screen that has a contrast ratio no less than 400:1 and a resolution no less than the resolution of the video camera, using signals transmitted directly from the video camera; and visually reviewing the enlarged digital image, and identifying an indication of a dental condition, or accessing dental information, revealed by the enlarged digital image.

The dental condition includes tooth caries, bone fracture, bone loss due to periodontal disease, or abscess in jaw or surrounding tissue. Furthermore, accessing dental information can include identifying a nerve location in a tooth, reviewing a bone or gum healing status, or identifying or confirming an implant location or condition.

Moreover, the method further includes monitoring a treatment of the dental condition by reviewing the intra-oral x-ray film obtained before and during or after the treatment, using the above described steps.

The advantages of the present invention will become apparent from the following description taken in conjunction with the accompanying drawings showing the exemplary embodiments of the invention.

BRIEF DESCRIPTION OF THE DRAWINGS

FIG. 3 is a perspective view of the film seat of the film illumination station of FIG. 2.

FIG. 4 is a partial cut-out side view of the illumination housing showing the film seat.

FIG. 4A is an enlarged cross sectional view of the film seat of the illumination housing shown in FIG. 4.

FIGS. 5 and 5A are top views of the film illumination station of FIG. 2, with and without an intra-oral x-ray film on the film window.

It is noted that in the drawings like numerals refer to like parts throughout.

DETAILED DESCRIPTION OF THE INVENTION

In one aspect, the present invention provides a dental X-ray film viewing device for displaying a substantially enlarged digital image of a standard intra-oral x-ray film for diagnosis, education, and communication with patients.

Figure 1:
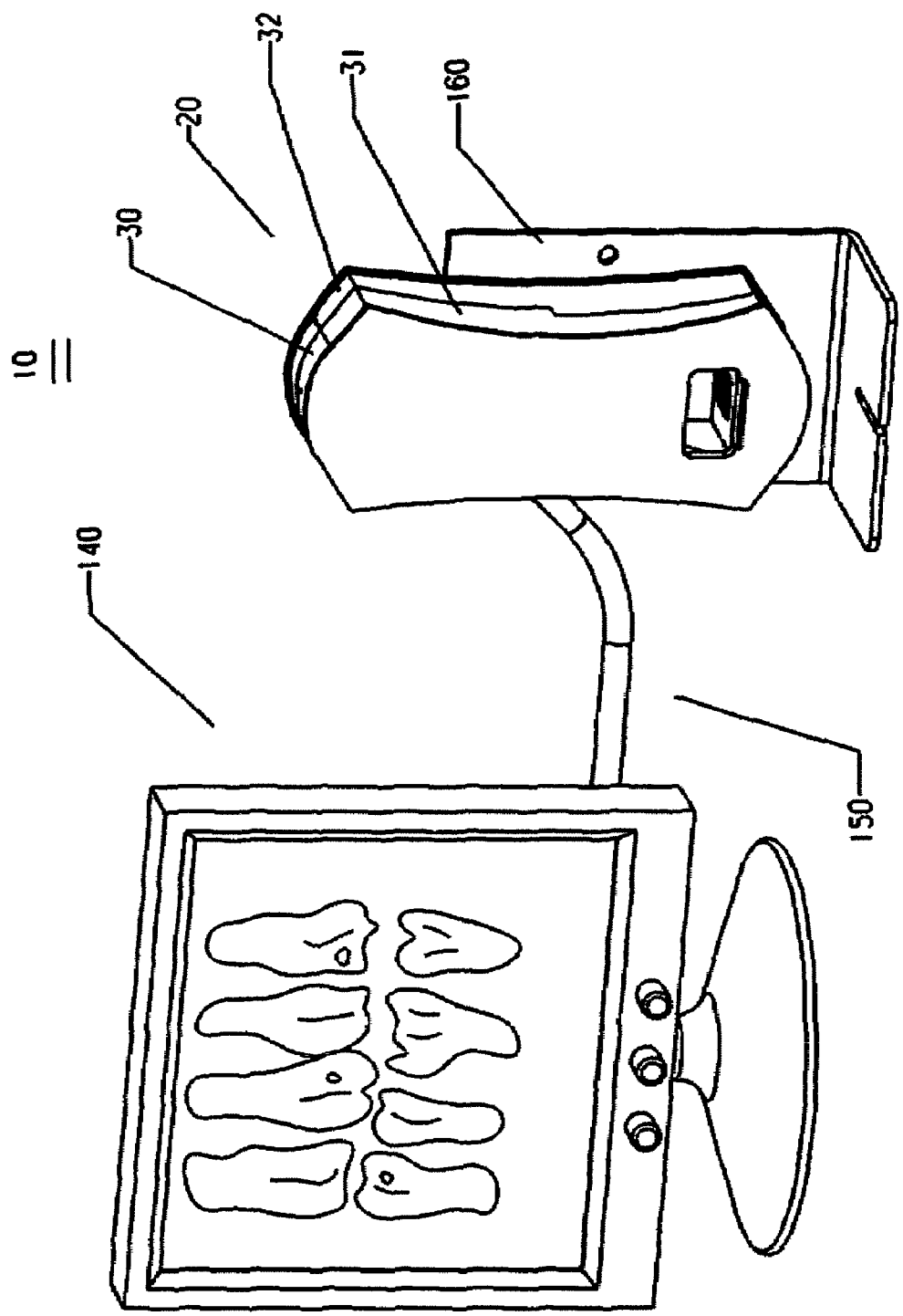
FIG. 1 is a perspective view of the dental x-ray film viewing device of one embodiment of the present invention.

In one embodiment, the dental X-ray film viewing device 10 of the present invention comprises a film reader 20 and an image display screen 140, interconnected by cable 150, as shown in FIG. 1.

Referring to FIGS. 1 to 9, film reader 20 comprises a system housing 30, a support panel 40 disposed inside system housing 30, a film illumination station 60 attached to lower portion 44 of support panel 40, and a video camera 120 attached to upper portion 42 of support panel 40.

Figure 2:
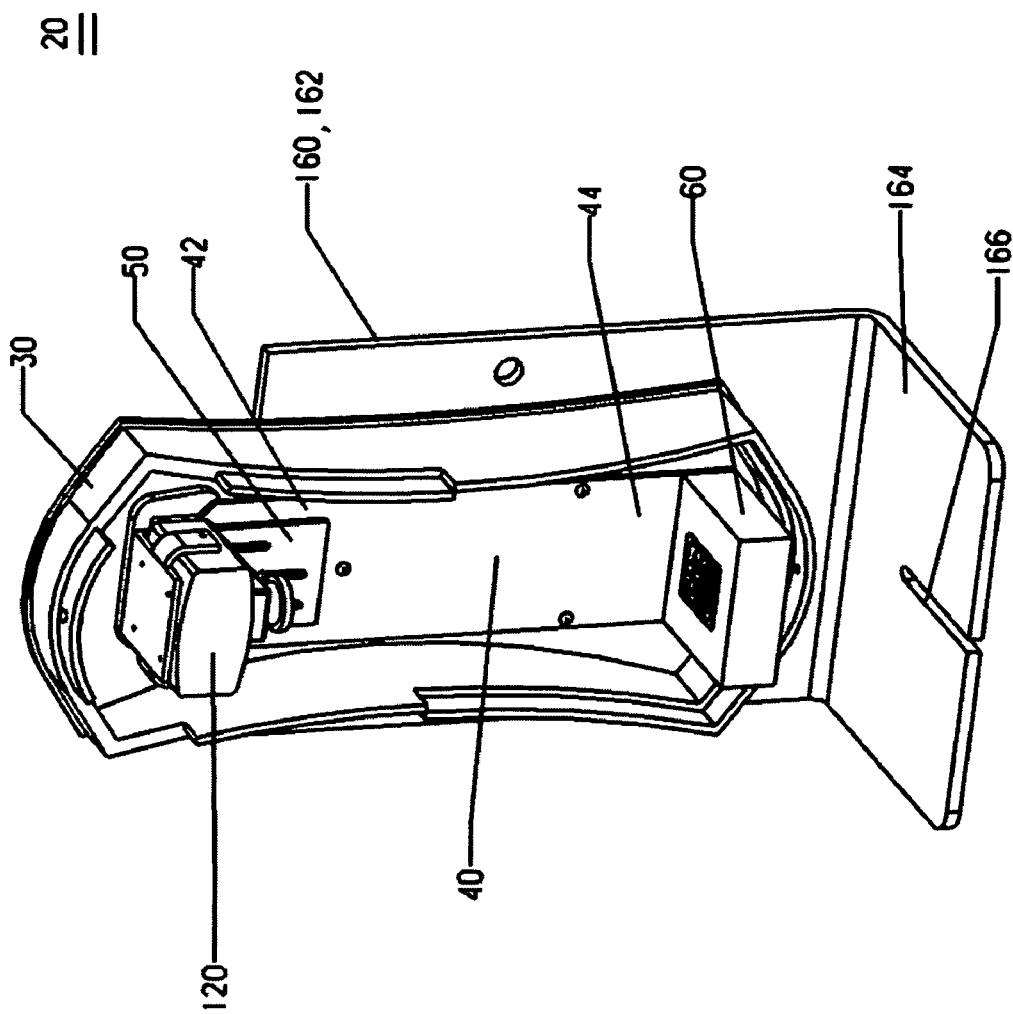
FIG. 2 is an elevated front view of the film reader of the dental x-ray film viewing device of FIG. 1, without the front panel.
Figure 8:
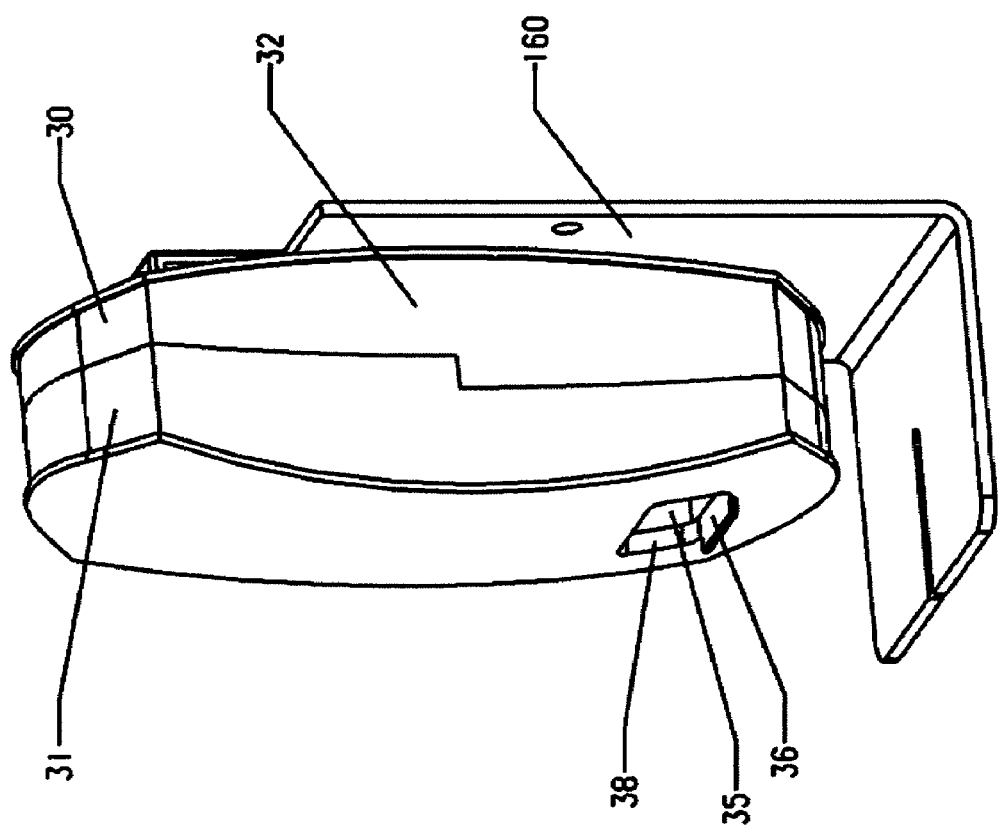
FIG. 8 is a perspective view of the film reader of the dental x-ray film viewing device of FIG. 1.

As shown in FIGS. 1, 2 and 8, in the specific embodiment shown system housing 30 includes a front panel 31 and a rear panel 32. System housing 30 is attached to a mount 160, which includes a wall mount portion 162 and a stand portion 164. Film reader 20 can be either mounted on a wall by securing wall mount portion 162 to the wall, or can stand on a counter top or a desk. Stand portion 164 of mount 160 can be further secured to the counter top using fasten means through slot 166 provided on the stand portion. It should be understood that system housing can also have other suitable structures. For example, the housing can have a flat base suitable for placing on a counter top, and has integral side and back panels with a removable front panel or a front door.

The film illumination station 60 comprises an illumination housing 62, a film seat 70 on a top panel 64 of illumination housing 62, and a diffused white light source 110 disposed within illumination housing 62 for backlighting film seat 70.

As shown in FIGS. 3 to 5A, film seat 70 comprises a translucent plate 80 and a non-transparent film anchoring wafer 90 attached to, or seating on top of, translucent plate 80. Non-transparent film anchoring wafer 90 is in a shape of frame, having an inner opening 92, which forms a translucent film window 100 for seating a x-ray film 200. Inner opening 92 is complimentary to an intra-oral x-ray film. The intra-oral x-ray film has two standard sizes in dentistry: 1 inch by 1.25 inch (1"×1.25") and 1 inch by 3 inch (1"×3"). Preferably, the dimensions of inner opening 92 are substantially equivalent to, yet complimentary to, the dimensions of the standard intra-oral x-ray film, either 1"×1.25", or 1"×3". With such a structure, film anchoring wafer 90 serves two functions. First, it serves as an anchoring device to fix the x-ray film within film window 100. Second, it serves as a mask to block the backlighting from light source 110 to emit from the area surrounding the x-ray film. The light emitted from the surrounding area is a stray light directing to the camera, which affects the contrast of the enlarged digital image on the display screen. By providing a light-tight fit of the x-ray film within inner opening 92, the quality of the produced digital image using the device of the present invention is assured. More specifically, by blocking the light from the light source in the area surrounding the x-ray film and at the interface between film anchoring wafer 90 and the x-ray film, the enlarged image has a substantially better contrast at the distal portions of the enlarged digital image. Consequently, the obtained enlarged digital image has substantially equivalent contrasts between the center and the distal portions of the image. Herein, a distal portion of the image refers to a portion near an edge of the produced image.

The object to be enlarged by the instant device is the standard intra-oral x-ray film used in dentistry, with a size of either 1"×1.25", or 1"×3". The method of producing an intra-oral x-ray film and the quality requirement are known to those of ordinary skilled in the art.

Film anchoring wafer 90 can be made of a solid non-transparent material, such as a metal sheet or a plastic sheet. In one embodiment, film anchoring wafer 90 is made of a metal sheet of about 0.4 mm thickness. The standard intra-oral x-ray film typically has a thickness about 0.2 mm. Preferably, film anchoring wafer 90 is thicker than the intra-oral x-ray film. The intra-oral x-ray film can be conveniently placed within film window 100, and can also be easily removed by hand through film access opening 35 of the front panel 31. FIGS. 1 and 7 to 9 show film access opening 35 on the front panel 31. At the lower end of film access opening 35, there is a platform 36 for supporting the hand. The top panel 64 of illumination housing 62 is aligned substantially on the same plane with platform 36 for the convenience of handling the x-ray film. In comparison to mechanically loading and unloading the film, manual operation in placing the x-ray film in and removing it from the device has the advantage of minimum moving components within the device. This provides lower instrument and maintenance costs and higher reliability.

Figure 7:
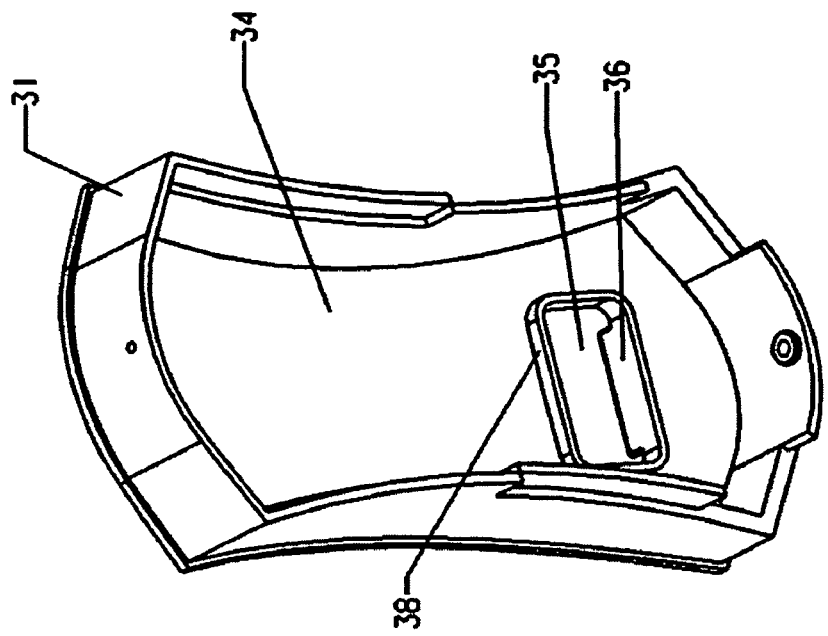
FIG. 7 is a perspective rear view of the front panel of the film reader, showing the film access opening, and the light shielding rim surrounding the opening.

As shown in FIGS. 7 and 8, there is a light shielding rim 38 on the rear side 34 of front panel 31 surrounding film access opening 35. Light shielding rim 38 is a rim protruding toward the interior of system housing 30. It can be an integral part of the housing, or a separate rim attached around film access opening 35. In an exemplary embodiment, light shielding rim 38 is an integral part of the housing produced by plastic molding, and it has a depth about 1.3 cm. Light shielding rim 38, particularly the upper portion thereof, blocking the stray light outside of the housing from shedding on the camera. It has been found that using a light shielding rim the interference from the stray light can be sufficiently prevented, without closing film access opening 35, with a door or other suitable means, during the use of the device. However, it can be appreciated that the film access opening can also be closed by a door or other suitable means when viewing the x-ray film. In such an alternative structure, light shielding rim is no longer needed.

It is noted that when the film reader described above is used in a dark room or in an environment that the stray light is sufficiently blocked, the housing is not required for obtaining high contrast images.

Translucent plate 80 is typically made of a translucent glass or plastic. The translucent plate used in the existing x-ray viewing boxes can be used for the purpose of the present invention. Preferably, diffused white light source 110 is a reflected cooled cathode fluorescent light (CCFL), or a set of white light emitting diodes (LEDs). Other suitable light source producing diffused white light can also be used for the purpose of the present invention.

In an exemplary embodiment, a circular reflected cooled cathode fluorescent light is used, which is mounted underneath top panel 64 of illumination housing 62. The luminous intensity of the CCFL at the location of the X-ray film is about 14,000 cd. If multiple LEDs are used as the diffused white light source, the luminous intensity of the LEDs at the location of the X-ray film is preferably no less than 20,000 cd. The luminous intensity of the diffused white light source at the location of the X-ray film can be optimized by adjusting the distance of the light source to the X-ray film, to achieve the desired contrast of the enlarged digital image that is suitable for diagnosis. It is noted that if the luminous intensity is too high, the desired contrast of the enlarged image would not be maintained. On the other hand, if the luminous intensity is too low, shadows of the light bulbs would be generated at the location of the X-ray film, which could be confused with dental features, such as fractures and decays, on the enlarged digital image. Therefore, the luminous intensity of the diffused white light source at the location of the X-ray film should be adjusted properly to avoid the problems described above.

Figure 6:
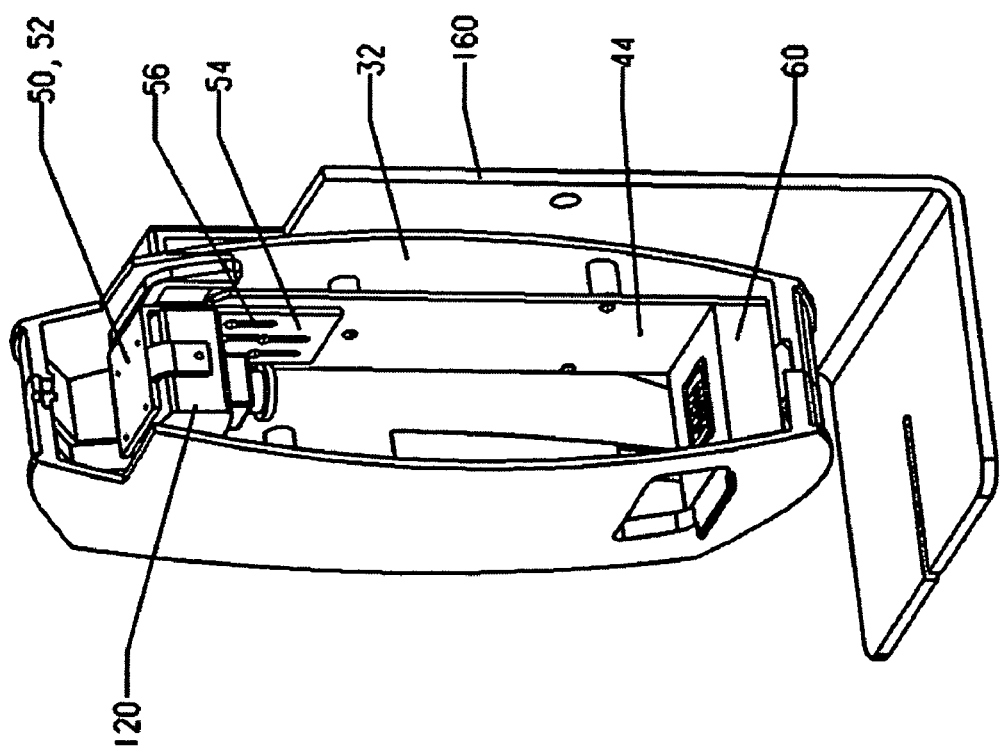
FIG. 6 is a cut-out perspective view of the film reader of FIG. 2, showing the attachment of the support panel to the housing and the attachment of the camera bracket to the support panel.
Figure 9:
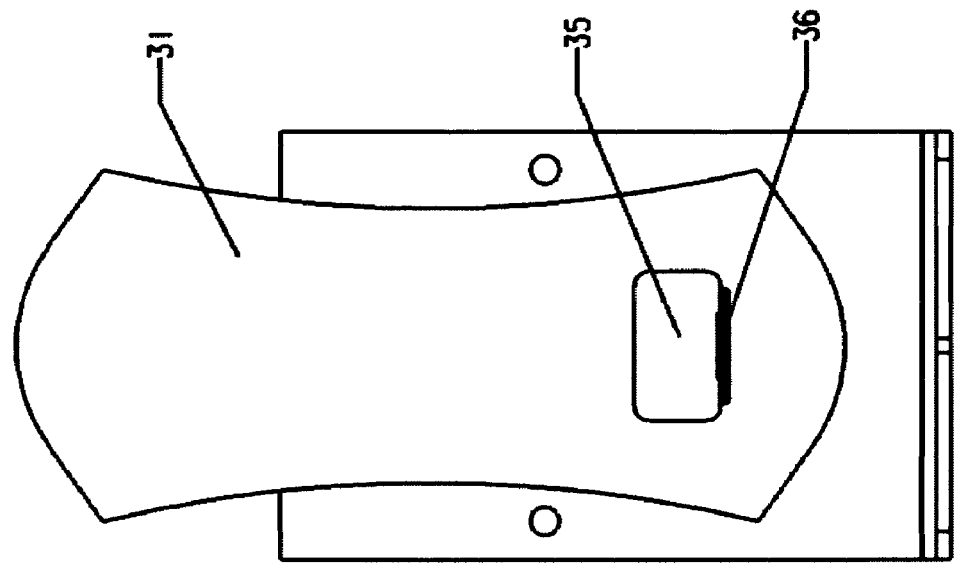
FIG. 9 is a front view of the film reader of the dental x-ray film viewing device of FIG. 1.

As shown in FIG. 6, camera 120 is mounted to a camera bracket 50. Camera bracket 50 has an upper portion 52 and a back panel 54 which has one or more grooves 56. Camera bracket 50 is attached to upper portion 42 of support panel 40 by fasten means through grooves 56. Camera bracket 50 can be adjusted vertically relative to film station 60, by sliding along grooves 56, to achieve required working distance for focusing between camera 120 and a x-ray film placed within film window 100. Other suitable mechanisms can also be used for adjusting the working distance of camera 120 for the purpose of the present invention. For example, the support panel can have grooves, and a camera body attached to engagement means complementary to the grooves can be slid along the grooves.

To ensure the stability of the device for maintaining focus, preferably, support panel 40 is firmly attached to system housing 30. In the embodiment shown in FIG. 6, support panel 40 is fastened to rear panel 32. Film illumination station 60 is mounted to lower portion 44 of support panel 40. When the working distance is adjusted for focus by the manufacturer or at the time of installation in the dentist's office, only camera bracket 50 is moved vertically to achieve the required focus. Herein, the term working distance refers to a specific distance between the lens of the camera and the x-ray film, which enables focusing of the lens.

Video camera 120 can be a CCD (charged coupled device) camera, or a CMOS (complimentary metal oxide semiconductor) camera. Camera lens 122 is directed to film window 100, with the center of camera lens 122 and the center of film window 100 aligned with each other. In an exemplary embodiment, a micro CCD board camera produced by Samsung is used. The micro CCD board camera comprises a CCD camera, a M-mount adaptor and a micro video lens. In the exemplary embodiment, a Edmundoptics' infinite conjugate MVO® µ-Video™ imaging lens having a focal length of 25.0 mm is used.

It should be understood that although various lenses can be used for producing enlarged digital images, the quality of the obtained image can be substantially different in terms of image distortion. Therefore, many enlarged digital images are not suitable for the purpose of dental diagnosis. Herein, image distortion is a geometric optical error (aberration) in which information about the object is misplaced in the image, but not actually lost. Using certain measurement software and a dot target of known size, the distortion at different distances from the center of the image can be measured using the equation:

$$\text{Distortion } (\%) = \frac{\text{Actual Distance } (AD) - \text{Predicted Distance } (PD)}{\text{Predicted Distance } (PD)} \times 100$$

It is further noted that distortion is not linearly correlated to the distance from the center of the field. Therefore, distortion is measured for each point on the image. Once the amount distortion is calculated, the distortion can be corrected in the design of the CCD camera by the manufacturers. Various methods known to those skilled in the art can be used for correcting the distortion. The resulting image is a precise representation of the original object. The manufacturer can provide the parameter of distortion at full field for each lens as one of the characteristics of the lens.

In general, the longer the focal length of a lens, the lower the distortion at full field is. For example, in a series of infinite conjugate MVO® µ-Video™ imaging lens from Edmundoptics, the micro video lenses having a focal length of 12.0 mm and 25.0 mm have a distortion at full field less than –1%. In comparison, the same type of micro video lenses having focal length between 1.7 mm and 2.5 mm can have the distortion at full field between –40% to –60%.

As described above, in an exemplary embodiment of the present invention, Edmundoptics' infinite conjugate MVO® µ-Video™ imaging lens having a focal length of 25.0 mm is used. This micro video lens has a distortion at full field of –0.46%, and a minimum working distance of 200 mm. In the exemplary embodiment, the working distance is set at about 235 mm. Among this series of lenses, the lens having a focal length of 12.0 mm has a distortion at full field of –0.15%, and a minimum working distance of 800 mm. For compactness of the film reader for a dentist office, the 25.0 mm lens is more preferably chosen. It should be understood, however, that the focal length, working distance, and the distortion at full field of a lens can vary depending on the construction of the lens by a specific manufacturer. Therefore, the relationship among focal length, working distance, and distortion at full field described above is applicable within this specific series of commercial products, and should not be construed as limiting for the purpose of the present invention. More importantly, for the purpose of achieving a substantially enlarged digital image with an accurate representation of the original image of an intra-oral x-ray film, preferably a lens of the video camera in the instant device has a distortion at full field less than 3%, more preferably, less than 1%.

Furthermore, it has been found that to produce an enlarged digital image of an intra-oral x-ray film adequate for diagnosis purpose using signals directly transmitted by the video camera, preferably the video camera has a resolution of at least 512×582 pixels.

Preferably, the image display screen is a flat screen monitor that has a resolution no less than the resolution of the video camera, and preferably has a contrast ratio no less than 400:1. Various commercially available LCD monitors can be used for the purpose of the present invention, for example, 15 inch or 17 inch LCD monitor, which are commonly used in the office. In an exemplary embodiment, a 15 inch LCD monitor having a television line horizontal resolution of 540 lines and a contrast ratio of 400:1 is used. Image display screen 140 is connected to video camera 120 by a composite video cable 150.

Using these monitors, an intra-oral x-ray film can be displayed as an enlarged digital image with an enlargement ratio of 75:1 to 150:1. The enlargement ratio described herein is expressed using square inch versus square inch (in$^2$:in$^2$), which is typically used in the measurement of image enlargement. For example, using a 15 inch monitor, the enlargement ratio of a 1"×1.25" dental x-ray film is enlarged 86.4 times. It is noted that theoretically, much larger monitors can be used for displaying the enlarged digital image, as long as the resolution of the monitor is no less than the resolution of the video camera. However, if the monitor is too large, for example, a 50 inch monitor, the image can be blurred when the same numbers of pixels are displayed on the substantially larger screen. On the other hand, from a practical stand point, based on a typical dental office setting, those commonly used LCD monitors, such as 15 inch to 19 inch monitors, are adequate displaying screens, which provide sufficient resolution and contrast of the image for diagnosis. With the achieved ratio of enlargement as described above, the enlarged digital image reveals sufficient information for the purpose of diagnosis, as further described hereinafter.

Because of the high quality in resolution and contrast, and a minimum distortion at the full field, the enlarged digital image produced by the device of the present invention can be used for education and communication with patients, and more importantly, for the purpose of diagnosis. Previously, many important details in a dental condition needed for diagnosis or monitoring a treatment are difficult to be recognized or to be confirmed by the standard intra-oral x-ray films because of their small size. On the other hand, the quality and reliability of the information provided by recently emerged post digital processing of x-ray film or direct intra-oral x-ray image still remain as a question in the diagnosis of dental diseases. The quality and reliability of post processed digital image depend on the algorithm and software used by the computer, which are currently designed by individual manufacturers, without an established standard or regulation in the dental industry. In addition to the software, the direct intra-oral x-ray image equipment further depends on the sensor or sensor material, and moreover, this method tends to have an inherent distortion. Because of these variables, it is difficult to obtain information which is consistent and reliable for diagnosis and for monitoring small improvements during medical treatment.

For the purpose of diagnosis, preferably the enlarged digital image produced using the device of the present invention includes an entirety of an intra-oral x-ray film. Therefore, it enables the dentist reviewing the entire x-ray film without moving or adjusting position of the x-ray film. As described above, on a 15 inch monitor, the image is enlarged 86.4 times. It has been found that because of the minimum distortion at the full field, the enlarged image produced by the instant device has a substantially equivalent quality between a central portion and distal portions of the image. Furthermore, because of effective blocking of the light in the area surrounding the x-ray film by the film anchoring wafer, the enlarged digital image also has a substantially equivalent contrast between a central portion and distal portions of the image.

Table 1 provides a comparison of the information revealed by the standard intra-oral x-ray films without enlargement and the enlarged digital images of the same films produced using the device of the present invention and displayed on a 15" LCD monitor. The un-enlarged image is displayed on a Kodak handheld film reader. The measurements of pathosis and normal landmarks of teeth and tissue are made using duplicate films.

TABLE 1

| Measurement | Image on Kodak ™ Handhold Film Reader | Image on the Instant Device |
| --- | --- | --- |
| Width periodontal ligament space - ⅓ apically from crestal bone | 0.25 mm | 1.15 mm |
| Width of mandibular canal | 5.1 mm | 44.7 mm |
| Size of carious lesion mesial 2nd molar | 0.14 mm × 0.15 mm | 6.6 mm × 8.1 mm |
| Bone loss at distal biscuspid "check shape" | 1.1 mm × .48 mm | 5.67 mm × 14.93 mm |
| Radiolucency at apex biscuspid | 0.11 mm × 0.01 mm | 13.59 mm × 6.91 mm |
| Width of canal middle of bicuspid | 0.41 mm | 8.53 mm |

It is noted that the fine outlines of pathosis are not apparent or readily visible on the Kodak™ Handhold Film Reader, however, these can be clearly recognized on the enlarged, high resolution and high contrast image produced by the device of the present invention. Furthermore, the larger the pathosis is, the lower the relative imprecision of a measurement.

Therefore, as a further aspect, the present invention provides a method of diagnosis and monitoring treatment by producing a substantially enlarged image using the device of the present invention, and utilizing the information revealed by the enlarged image for identifying dental conditions, accessing dental information, and monitoring dental treatments. Herein, the dental conditions include, but are not limited to, tooth caries, bone fracture, bone loss due to periodontal disease, or abscess in jaw or surrounding tissue. In addition to identifying dental conditions, accessing dental information can include, but is not limited to, identifying a nerve location in a tooth, reviewing a bone or gum healing status, or identifying or confirming an implant location or condition.

As an example, as shown in Table 1, the size of a carious lesion at mesial second molar is only 0.14 mm×0.15 mm. A lesion of such a size is frequently missed by the dentists. Even if the lesion is not entirely missed, as the lesion is so small that renders the judgment extremely difficult. In contrast, using the image produced by the instant device, the same lesion is shown with a dimension of 6.6 mm×8.1 mm. This can be easily recognized visually with certainty; therefore, the lesion can be treated timely.

The instant method is particularly suitable for monitoring a dental treatment. A dental condition can be reviewed before, during and after a specific treatment. Sometimes, upon treatment a dental condition improves gradually, which can be over a substantial period of time. For example, bone and gum healing is a slow process. At each follow up examination, it is important for the dentist to assess the patient's response to the treatment. However, as the change may not be substantial between two examinations, it is difficult to assess a small improvement using the information revealed by the standard x-ray film without enlargement. Using the instant device, small incremental changes can be recognized early, which can effectively help the dentist in making timely decisions, for example, continuing or changing the treatment protocol.

It is important to understand that using the device of the present invention the enlarged digital image of the x-ray film displayed on image display screen 140 is obtained using signals transmitted directly from CCD camera 120, without post digital processing. This is fundamentally different from the existing methods of digital image processing and displaying. As described above, the quality and reliability of the information provided by post digital processing of x-ray film or direct intra-oral x-ray image still remain as a question in the diagnosis of dental diseases, because of their reliance on the software, such as post processing smoothing algorithms, used by the computer, as well as the sensors. These types of dental image instruments are complex and very expensive, which also require a substantial amount of training of the operator. However, none of these equipments has received approval from the Food and Drug Administration (FDA). In a typical dental office setting, there are multiple rooms for examination and treatment of patients; each room needs x-ray display equipment, such as the traditional x-ray film viewer box. It is impractical to install multiple dental image instruments in a dentist office at a cost of more than ten thousand dollar per instrument.

In contrast, the simplicity in instrumentation and methodology provided by the present invention provides various advantages for both manufacturing and the end users. It is easy to operate with minimum training, and reliable because of no moving components to be handled by the user. The instant device is inexpensive, having a cost about only a few percent of the dental image instruments described above. Furthermore, as no post digital processing is involved in the enlarged image obtained, it can be easily accepted by the dentists for diagnostic purposes.

More importantly, as described above, the enlarged digital image provided by the device of the present invention is an accurate reproduction of the original image on the standard intra-oral x-ray film. Different from the enlarged image produced using the device of prior art, the digital image provided by the instant device that utilizes a lens with a focal length of more than 20 mm has a minimum distortion at the full field.

The following examples are illustrative of the invention and are in no way to be interpreted as limiting the scope of the invention, as defined in the claims.

EXAMPLE 1

The performance of the instant dental x-ray film viewing device is evaluated against a Telerex Video x-ray film viewer using the standard 1"×1.25" intra-oral x-ray films.

The instant dental x-ray film viewing device has been described above. In this exemplary embodiment, a micro CCD board camera produced by Samsung, equipped with a Edmundoptics' infinite conjugate MVO® μ-Video™ imaging lens having a focal length of 25.0 mm is used. This micro video lens has a distortion at full field of −0.46%. The working distance is set at about 235 mm, which is substantially longer than that of Telerex. The prior art instrument has a height of 9.4 cm, and estimated working distance of the lens is less than 80 mm. A 15 inch LCD monitor is used as the display screen in the instant device.

Table 2 shows some of the characteristics of the instant device versus the prior art instrument. More specifically, resolution and diagnostic usefulness of the enlarged image, visibility of the entire x-ray film, and the ability of reviewing multiple teeth are compared.

As shown, the enlarged digital image provided by the device of the present invention provides required quality and sufficient information for the purpose of diagnosis. On the contrary, the image produced by the prior art instrument has a limited utility for diagnosis.

TABLE 2

|  | Telerex | Instant Device |
|---|---|---|
| Resolution | Distal portions are blurred | Substantially equivalent resolution of the entire image |
| Diagnostic usefulness | Distal portions of enlarged image can not be used | The entire enlarged image can be used |
| Visibility of entire film | Edges obstructed by the tray | Entire film is visible |
| Review of multiple teeth | Teeth at distal portion of the image can not be used | Review up to five teeth at once, including surrounding features |

The invention has been described with reference to particularly preferred embodiments. It will be appreciated, however, that various changes can be made without departing from the spirit of the invention, and such changes are intended to fall within the scope of the appended claims. While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A dental X-ray film viewing device comprising:
(a) a film reader comprising:
a support panel;
a film illumination station attached to a first end of said support panel, said film illumination station comprising an illumination housing, a film seat on a wall of said housing, and a diffused white light source disposed within said illumination housing for backlighting said film seat; said film seat comprising a translucent plate and a non-transparent film anchoring wafer disposed against said translucent plate, said film anchoring wafer having an inner opening complimentary to an intra-oral x-ray film thereby forming a translucent film window for seating said x-ray film within said film window, and said film anchoring wafer blocking light from said light source in an area surrounding said x-ray film; and
a video camera attached to a second end of said support panel, having lens thereof directed to a center of said film window of said film illumination station; said lens having a distortion at full field less than 3%; and
(b) an image display screen connected directly to said video camera of said film reader by a cable, adapted to display an enlarged digital image of said x-ray film using signals transmitted from said video camera directly to said image display screen.

2. The dental X-ray film viewing device of claim 1, wherein dimensions of said inner opening of said film anchoring wafer are substantially equivalent to dimensions of said intra-oral x-ray film.

3. The dental X-ray film viewing device of claim 1, wherein said lens of said video camera has a distortion at full field less than 1%.

4. The dental X-ray film viewing device of claim 1, wherein said video camera has a resolution of at least 512×582 pixels.

5. The dental X-ray film viewing device of claim 1, wherein a lens of said video camera has a working distance in a range from about 200 mm and about 400 mm.

6. The dental X-ray film viewing device of claim 1, wherein said image display screen is a LCD monitor having a resolution no less than the resolution of said video camera and a contrast ratio of at least 400:1.

7. The dental X-ray film viewing device of claim 1, wherein said enlarged digital image has an enlargement ratio from about 75:1 to about 150:1 ($in^2:in^2$).

8. The dental X-ray film viewing device of claim 1, wherein said enlarged digital image includes an entirety of said intra-oral x-ray film, has a substantially equivalent resolution and contrast between a central portion and a distal portion of said image, and a distortion at full field less than 3%.

9. The dental X-ray film viewing device of claim 1, wherein said diffused white light source is a reflected cooled cathode fluorescent light, or a set of white light LEDs.

10. A dental X-ray film viewing device comprising:
(a) a film reader comprising:
a system housing including a film access opening;
a support panel disposed within said system housing;
a film illumination station disposed within said system housing, attached to a lower portion of said support panel, said film illumination station comprising an illumination housing, a film seat on a wall of said housing, and a diffused white light source disposed within said illumination housing for backlighting said film seat; said film seat comprising a translucent plate and a non-transparent film anchoring wafer disposed against said translucent plate, said film anchoring wafer having an inner opening complimentary to an intra-oral x-ray thereby forming a translucent film window for seating said x-ray film within said film window, and said film anchoring wafer blocking light from said light source in an area surrounding said x-ray film; and
a video camera attached to an upper portion of said support panel, having lens thereof directed to a center of said film window of said film illumination station; said lens having a distortion at full field less than 3%; and
(b) an image display screen connected directly to said video camera of said film reader by a cable, adapted to display an enlarged digital image of said x-ray film using signals transmitted from said video camera directly to said image display screen.

11. The dental X-ray film viewing device of claim 10, wherein said film access opening has a light shielding rim surrounding said opening and protruding toward an interior of said system housing.

12. The dental X-ray film viewing device of claim 10, wherein said lens of said video camera has a distortion at full field less than 1%.

13. The dental X-ray film viewing device of claim 10, wherein said video camera has a resolution of at least 512×582 pixels.

14. The dental X-ray film viewing device of claim 10, wherein a lens of said video camera has a working distance in a range from about 200 mm and about 400 mm.

15. The dental X-ray film viewing device of claim 10, wherein said image display screen is a LCD monitor having a resolution no less than the resolution of said video camera and a contrast ratio of at least 400:1.

16. The dental X-ray film viewing device of claim 10, wherein said enlarged digital image has an enlargement ratio from about 75:1 to about 150:1 ($in^2:in^2$).

17. The dental X-ray film viewing device of claim 10, wherein said enlarged digital image includes an entirety of said intra-oral x-ray film, has a substantially equivalent resolution and contrast between a central portion and a distal portion of said image, and a distortion at full field less than 3%.

18. The dental X-ray film viewing device of claim 10, wherein said diffused white light source is a reflected cooled cathode fluorescent light, or a set of white light LEDs.

19. A method of producing an enlarged digital image of an intra-oral x-ray film comprising the steps of:
  (a) placing an intra-oral x-ray film on a translucent film window complementary in dimensions to said x-ray film, and backlighting said film window with a diffused white light source; said film window being surrounded by a non-transparent material to substantially block light from said light source in an area surrounding said x-ray film;
  (b) positioning a video camera with a lens thereof directing to a center of said x-ray film, said lens having a distortion at full field less than 3% and said video camera having a resolution of at least 512×582 pixels; and
  c) displaying a substantially enlarged digital image of said x-ray film on an image display screen having a resolution no less than the resolution of said video camera, using signals transmitted from said video camera directly to said image display screen.

20. The method of claim 19, wherein said enlarged digital image includes an entirety of said intra-oral x-ray film, with an enlargement ratio of about 75:1 to 150:1 ($in^2:in^2$).

21. The method of claim 19, wherein said enlarged digital image has a substantially equivalent resolution and contrast between a central portion and a distal portion of said image, and a distortion at full field less than 3%.

22. A method of dental diagnosis comprising the steps of:
  (a) providing an intra-oral x-ray film;
  (b) focusing a lens of a video camera on said x-ray film; said lens having a distortion at full field less than 3%; and said video camera having a resolution of at least 512×582 pixels;
  (c) displaying a substantially enlarged digital image of said x-ray film on an image display screen that has a contrast ratio no less than 400:1 and a resolution no less than the resolution of said video camera, using signals transmitted from said video camera directly to said image display screen; and
  (d) visually reviewing said enlarged digital image, and identifying an indication of a dental condition, or accessing dental information, revealed by said enlarged digital image.

23. The method of claim 22 further comprising monitoring a treatment of said dental condition by reviewing said intra-oral x-ray film obtained before and during or after said treatment, using the steps of (a) thru (c).

24. The method of claim 22, wherein said dental condition comprises tooth caries, bone fracture, bone loss due to periodontal disease, or abscess in jaw or surrounding tissue.

25. The method of claim 22, wherein said accessing dental information comprises identifying a nerve location in a tooth, reviewing a bone or gum healing status, or identifying or confirming an implant location or condition.

26. A dental X-ray film viewing device comprising:
  (a) a film reader comprising:
  a support panel;
  a film illumination station attached to a first end of said support panel, said film illumination station comprising an illumination housing, a film seat on a wall of said housing, and a diffused white light source disposed within said illumination housing for backlighting said film seat; said film seat comprising a translucent plate and a non-transparent film anchoring wafer disposed against said translucent plate, said film anchoring wafer having an inner opening complimentary to an intra-oral x-ray film thereby forming a translucent film window for seating said x-ray film within said film window, and said film anchoring wafer blocking light from said light source in an area surrounding said x-ray film; and
  a video camera attached to a second end of said support panel, having lens thereof directed to a center of said film window of said film illumination station; and
  (b) an image display screen connected directly to said video camera of said film reader by a cable, adapted to display an enlarged digital image of said x-ray film using signals transmitted from said video camera directly to said image display screen.

* * * * *